United States Patent [19]

Landis et al.

[11] 4,104,181

[45] Aug. 1, 1978

[54] ADDITIVES COMPRISING (N, N-DIORGANOTHIOCARBAMYL) PHOSPHOROTHIOITES AND LUBRICANT COMPOSITIONS CONTAINING THE SAME

[75] Inventors: Phillip S. Landis, Woodbury; Abraham O. M. Okorodudu, West Deptford, both of N.J.

[73] Assignee: Mobil Oil Corporation, New York, N.Y.

[21] Appl. No.: 834,368

[22] Filed: Sep. 19, 1977

[51] Int. Cl.² .......................... C10M 1/48; C10M 3/42; C10M 5/24; C10M 7/46
[52] U.S. Cl. ................................ 252/46.7; 260/545 P; 260/935
[58] Field of Search ................... 252/46.7; 260/545 P, 260/935

[56] References Cited

U.S. PATENT DOCUMENTS 2,743,235  4/1956  McDermott ...................... 252/46.7

Primary Examiner—Irving Vaughn
Attorney, Agent, or Firm—Charles A. Huggett; Raymond W. Barclay; Howard M. Flournoy

[57] ABSTRACT

Novel (N, N-diorganothiocarbamyl) phosphorothioites having the following general structures:

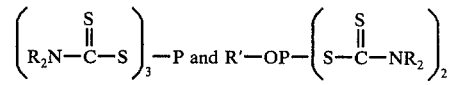

and mixtures thereof impart good antiwear and EP properties to lubricant compositions (e.g. gear oils and cutting oils) containing them.

26 Claims, No Drawings

ADDITIVES COMPRISING (N, N-DIORGANOTHIOCARBAMYL) PHOSPHOROTHIOITES AND LUBRICANT COMPOSITIONS CONTAINING THE SAME

BACKGROUND OF THE INVENTION

1. Field of the Invention

This application is directed to load-carrying or antiwear additives comprising certain novel (N, N-diorganothiocarbamyl) phosphorothioites and their synthesis and to lubricant compositions containing same.

2. Summary of the Prior Art

Organic sulfur compounds are known additives for lubricant compositions wherein they provide extreme pressure and antiwear protection. However, high sulfur content additives tend to have solubility problems with respect to some lubricant base stocks as well as tending to cause the corrosion of metal parts with which they contact.

SUMMARY OF THE INVENTION

It has now been discovered that the reaction products of certain phosphorous di- and triamides with carbon disulfide exhibit good load-carrying and antiwear activity. So far as is known, no previous art exists which discloses or suggests the hereinembodied novel reaction products or their use as load-carrying or antiwear additives when the same are incorporated into lubricant compositions.

The additives in accordance with this invention may be conveniently prepared by reacting a suitable phosphorous amide with carbon disulfide. The resultant reaction product is thereafter incorporated into a mineral or synthetic lubricating oil. Accordingly this application is concerned with lubricant compositions comprising a major amount of an oil of lubricating viscosity or a grease utilizing said oil as the vehicle and a minor amount sufficient to impart load-carrying properties to said lubricant composition of a compound selected from:

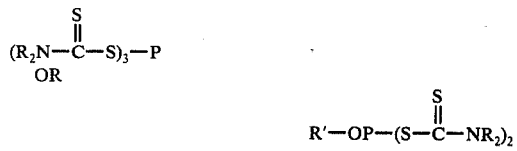

or mixtures thereof, where R and R' are alkyl of 1 to about 32 carbon atoms, aryl of 6 to 32 carbon atoms or alkaryl of 7 to 32 carbon atoms R and R' may be but are generally not the same. This application is further specifically directed to said phosphorus-sulfur-nitrogen containing materials as novel compounds.

DESCRIPTION OF SPECIFIC EMBODIMENTS

As previously noted the additive compounds may be prepared by reacting phosphorous amides with carbon disulfide. Any suitable phosphorous di- or triamide may be conveniently used in this reaction. Preferably, the phosphorous amide has one of the following structures $(R_2N)_3P$ or $R'OP(NR_2)_2$ where R and R' are as defined above. R and R' also may be alicyclic $(C_nH_{2n-1})$ such as in cyclopentyl $(C_5H_9-)$ or cyclohexyl $(C_6H_{11}-)$ and R may be $(CH_2)n$ comprising the hydrocarbyl part of a heterocyclic system such as $-(CH_2)_4-$ in pyrolidine or $-(CH_2)_5-$ in piperidine.

The phosphorous amides useful herein may be commercially obtained or prepared via the following general reactions:

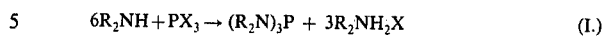

any suitable halide (X) may be used, i.e., chloro, bromo or iodo.

The novel additive compounds can then be readily prepared in good yield in accordance with the following general equations:

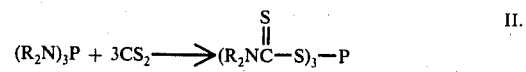

The reaction conditions of Equation I are conventional in the art.

General reaction conditions for Equation II are as follows: To a solution of the organo phosphorous triamide in benzene (or any suitable solvent) a stoichiometric amount or slight excess of carbon disulfide is added dropwise at a rate suitable to moderate the exothermic reaction. After the addition, the reaction mixture is heated briefly at reflux, cooled, and the product isolated.

The reaction conditions for Equation III are usually the same as for II, except that a stoichiometric amount of $R'OP(NR_2)_2$ is used.

As previously stated hereinabove, R and R' are hydrocarbyl containing up to 32 carbon atoms which can be alkyl, aromatic or alkyl-substituted aromatic and wherein the alkyl groups include methyl, octyl, decyl, dodecyl, tetradecyl and the like. The disclosure of these groups is disclosure thereof in all the various final products of this invention.

The additives in accordance with this invention are effectively used in lubricant compositions in which the lubricant base is a petroleum product, such as a mineral lubricating oil or a synthetic fluid. The synthetic fluids include synthetic hydrocarbons derived from long chain alkanes or olefin polymers, ester oils obtained from polyhydric alcohols and monocarboxylic acids or monohydric alcohols and polycarboxylic acids. The lubricants include grease prepared from the fluids described above.

The concentration of the additive compounds may vary from about 0.05 to about 10% or more by weight. Lubricant compositions containing them preferably have from about 0.25 to about 2% by weight of the additive based on the total weight of the composition.

EXAMPLE 1

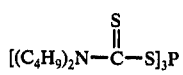

was prepared as follows:

Benzene (150 ml) and hexabutylphosphorous triamide (120 g, 0.29 moles) were charged into a reaction flask and carbon disulfide (132 g, 1.7 moles) added dropwise over a 30 minute period. The reaction mixture was then refluxed for 2 hours and cooled. Upon standing, solids separated which were collected and washed with petroleum ether. Product, m.p. 117°-120°, 6.9% nitrogen (calc. 6.5%), and 5.3% phosphorous (calc. 4.8%).

EXAMPLE 2

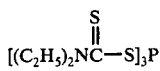

was prepared as follows:

Hexaethylphosphorous triamide (100 g, 0.4 moles) and 200 ml of benzene were charged into a reaction flask and stirred. To this, carbon disulfide (185 g, 2.4 moles) was added dropwise over a 30 minute period controlling the exothermic reaction temperature at around 40° C. Following the addition, the mixture was refluxed for 30 minutes and cooled. Solids which separated were collected, washed with benzene and air dried. The product contained 6.7% phosphorous (calc. 6.4%) and 8.9% nitrogen (calc. 8.7%).

EXAMPLE 3

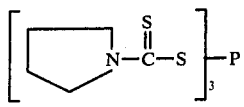

was prepared as in Example 2, except that tris tetramethylene phosphorous triamide was used. The product contained 7.7% phosphorous (calc. 6.5%).

EXAMPLE 4

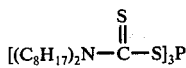

was prepared as in Example 2, except that tetraoctylphosphorous triamide was used. The liquid product obtained after stripping the reaction mixture contained 5.4% nitrogen (calc. 4.2% nitrogen).

EXAMPLE 5

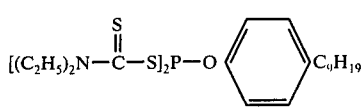

was prepared as in Example 2, 0.4 moles of nonylphenyl tetraethylphosphorous diamide and 0.8 moles of carbon disulfide were reacted. The product obtained after stripping the reaction mixture under vacuum contained 6% phosphorous (calc. 5.7%) and 4.9% nitrogen (calc. 5.1%).

EXAMPLE 6

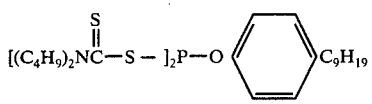

was prepared as in Example 2, except that nonylphenyl tetrabutylphosphorous diamide (0.5 moles) and 1.1 moles of carbon disulfide were used. The product, after stripping the reaction mixture under vacuum, contained 3.3% phosphorous (calc. 4.7%) and 5.3% nitrogen (calc. 4.3%).

The additive compounds of this invention were evaluated in a 4-Ball Wear Test using ½ inch 52100 Steel Balls at a load of 60 kg. for 30 minutes under the conditions set forth in Table I below. The oil used was an 80/20 mixture of a solvent refined mid-Continent paraffinic 150/160 second bright mineral oil and a 200/210 second refined mid-Continent neutral mineral oil.

Table II details data from a similar 4-Ball Wear Test using a synthetic ester lubricant made by reacting pentaerythritol with an equimolar mixture of $C_5$ and $C_9$ monocarboxylic acids.

TABLE I

| | 4-BALL WEAR SCAR DIAM (mm) ½" BALLS 52100 STEEL 60 Kg, 30 min. | | | | | | |
|---|---|---|---|---|---|---|---|
| | | Conc. | Temp. | SPEED (RPM) | | | |
| Example | Additive | Wt % | °F | 500 | 1000 | 1500 | 2000 |
| | Base Stock | | Room | 0.50 | 0.60 | 0.88 | 2.34 |
| | | | 200 | 0.60 | 1.06 | 1.86 | 2.23 |
| | | | 390 | 1.0 | 1.31 | 2.06 | — |
| 1. | [(C$_4$H$_9$)$_2$N—C(=S)—S]$_3$P | 1 | Room | 0.40 | 0.40 | 0.50 | 0.60 |
| | | | 200 | 0.40 | 0.55 | 0.60 | 0.75 |
| | | | 390 | 0.95 | 0.90 | 1.05 | 1.20 |
| 2. | [(C$_2$H$_5$)$_2$N—C(=S)—S—]$_3$P | 1 | Room | 0.40 | 0.40 | 0.50 | 0.70 |
| | | | 200 | 0.40 | 0.50 | 0.50 | 0.45 |
| | | | 390 | 0.45 | 0.70 | 1.10 | 1.30 |
| 3. | [N—C(=S)—S]$_3$P (tetramethylene) | 1 | Room | 0.40 | 0.60 | 0.65 | 1.40 |
| | | | 200 | 0.55 | 0.60 | 0.70 | 0.70 |
| | | | 290 | 0.60 | 0.80 | 1.05 | 1.90 |
| 4. | [(C$_8$H$_{17}$)$_2$N—C(=S)—S]$_3$P | 1 | Room | 0.45 | 0.60 | 1.70 | 0.90 |
| | | | 200 | 0.60 | 0.70 | 0.80 | 1.80 |
| | | | 390 | 0.90 | 1.0 | 2.35 | 2.0 |
| 5. | [(C$_2$H$_5$)$_2$N—C(=S)—S]$_2$P—O—C$_6$H$_4$—C$_9$H$_{19}$ | 1 | Room | 0.40 | 0.50 | 0.50 | 0.70 |
| | | | 200 | 0.50 | 0.50 | 0.55 | 0.50 |
| | | | 390 | 0.50 | 0.70 | 1.85 | 1.70 |

TABLE I-continued

4-BALL WEAR SCAR DIAM (mm)
½" BALLS 52100 STEEL 60 Kg, 30 min.

| Example | Additive | Conc. Wt % | Temp. °F | SPEED (RPM) | | | |
|---|---|---|---|---|---|---|---|
| | | | | 500 | 1000 | 1500 | 2000 |
| 6. | [(C$_4$H$_9$)$_2$N—C(=S)—S—]$_2$P—O—C$_6$H$_4$—C$_9$H$_9$ | 1 | Room | 0.40 | 0.50 | 0.50 | 0.50 |
| | | | 200 | 0.50 | 0.50 | 0.50 | 0.50 |
| | | | 390 | 0.50 | 0.60 | 0.85 | 0.90 |

TABLE II

4-BALL WEAR SCAR DIAM (mm)
½" BALLS 52100 STEEL 60 Kg, 30 min.

| Item | Additive | Conc. Wt % | Temp. °F | SPEED (RPM) | | | |
|---|---|---|---|---|---|---|---|
| | | | | 500 | 1000 | 1500 | 2000 |
| | Base Stock | | Room | 0.70 | 0.90 | 0.90 | 1.95 |
| | | | 200 | 0.80 | 0.90 | 2.0 | 2.10 |
| | | | 390 | 0.90 | 1.30 | 1.50 | 2.40 |
| 1. | [(C$_4$H$_9$)$_2$N—C(=S)—S]$_3$P | 1 | Room | 0.50 | 0.50 | 0.69 | 0.75 |
| | | | 200 | 0.50 | 0.53 | 0.50 | 1.75 |
| | | | 390 | 0.50 | 0.55 | 2.0 | 2.10 |
| 2. | [(C$_2$H$_5$)$_2$N—C(=S)—S—]$_3$P | 1 | Room | 0.50 | 0.70 | 0.80 | 1.75 |
| | | | 200 | 0.50 | 0.70 | 0.80 | 1.95 |
| | | | 390 | 1.0 | 1.0 | 2.10 | 2.0 |
| 3. | [cyclic-N—C(=S)—S—]$_3$ P | 1 | Room | — | — | — | — |
| | | | 200 | 0.70 | 0.70 | 0.80 | 1.85 |
| | | | 290 | 1.0 | 1.2 | 1.45 | 1.65 |
| 4. | [(C$_8$H$_{17}$)$_2$N—C(=S)—S]$_3$P | 1 | Room | 0.70 | 0.90 | 1.0 | 1.2 |
| | | | 200 | 0.90 | 1.0 | 1.20 | 2.0 |
| | | | 390 | 1.0 | 1.2 | 1.80 | 2.0 |
| 5. | [(C$_2$H$_5$)$_2$N—C(=S)—S]$_2$P—O—C$_6$H$_4$—C$_9$H$_{19}$ | 1 | Room | 0.60 | 0.60 | 0.70 | 1.60 |
| | | | 200 | 0.70 | 0.70 | 0.75 | 1.65 |
| | | | 390 | 0.70 | 1.30 | 1.15 | 1.60 |
| 6. | [(C$_4$H$_9$)$_2$N—C(=S)—S—]$_2$P—O—C$_6$H$_4$—C$_9$H$_9$ | 1 | Room | 0.40 | 0.60 | 0.60 | 0.80 |
| | | | 200 | 0.60 | 0.80 | 0.70 | 1.60 |
| | | | 390 | 0.70 | 1.0 | 1.0 | 2.15 |

The data of Tables I and II reveal that in general the reaction products in accordance with this invention (Examples 1 to 6) showed good antiwear/load-carrying properties.

Only preferred embodiments have been exemplified, however, variations are within the skill of the art. Departure therefrom is within the scope of this specification.

We claim:

1. A lubrication composition comprising a major amount of an oil of lubricating viscosity or grease prepared therefrom and a minor load-carrying amount of a compound selected from the group consisting of compounds of the following general formulae:

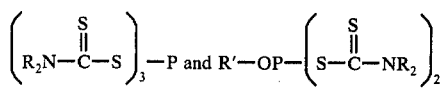

or mixtures thereof where R and R' are alkyl of 1 to 32 carbon atoms, aryl of 6 to 32 carbon atoms or alkaryl of 7 to 32 carbon atoms, and where R and R' are also selected from (C$_n$H$_{2n-1}$) where $n$ is from 3 to about 20 and R is also selected from (CH$_2$)$_n$ in heterocyclic systems with $n$ being from 2 to about 10.

2. The composition of claim 1 where said compound has the following general formula:

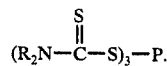

3. The composition of claim 2 where R is alkyl of from 1 to about 15 carbon atoms.

4. The composition of claim 3 where the compound is:

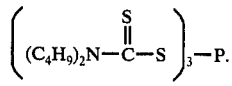

5. The composition of claim 3 where the compound is:

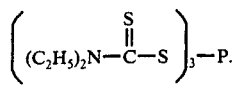

6. The composition of claim 3 where the compound is:

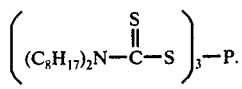

7. The composition of claim 1 where the compound is:

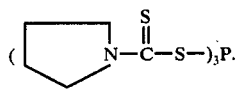

8. The composition of claim 1 where said compound has the following general formula:

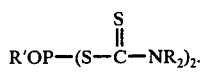

9. The composition of claim 8 where R is alkyl of from 1 to about 15 carbon atoms and R' is alkaryl of from 7 to about 20 carbon atoms.

10. The composition of claim 9 where the compound is:

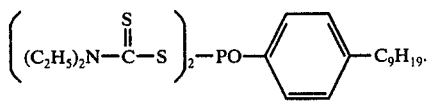

11. The composition of claim 9 where the compound is:

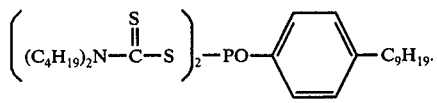

12. The composition of claim 1 where the oil of lubricating viscosity is a mineral oil.

13. The composition of claim 1 where the oil of lubricating viscosity is a synthetic oil.

14. The composition of claim 1 where the amount of said compound therein varies from about 0.05–10 wt. % based on the total weight of the composition.

15. The composition of claim 14 where the amount of the compound therein varies from about 0.25–2 wt. % based on the total weight of the composition.

16. A compound selected from the groups consisting of compounds of the following general structure:

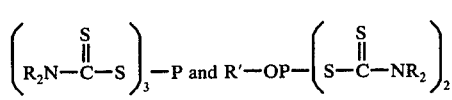

where R and R' are alkyl of 1 to about 32 carbon atoms, aryl of 6 to 32 carbon atoms or alkaryl of 7 to 32 carbon atoms and where R and R' are also selected from $(C_nH_{2n-1})$ where $n$ is from 3 to 20 and R may be selected from $(CH_2)_n$ in heterocyclic systems where $n$ is from 2 to 10.

17. The compound of claim 16 where said compound has the following general structure:

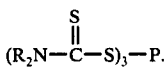

18. The compound of claim 17 where R is alkyl of 1 to about 15 carbon atoms.

19. The compound of claim 18 where the compound is:

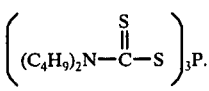

20. The compound of claim 18 where the compound is:

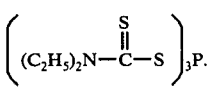

21. The compound of claim 18 where the compound is:

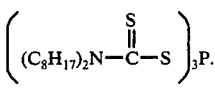

22. The compound of claim 16 where the compound is:

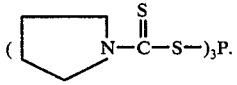

23. The compound of claim 16 where said compound has the following general formula:

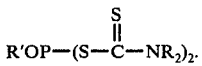

24. The compound of claim 23 where R is alkyl of from 1 to about 15 carbon atoms and R' is alkaryl of from 7 to about 20 carbon atoms.

25. The compound of claim 24 where the compound is:

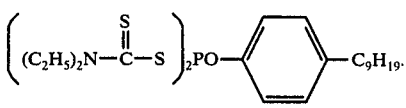

26. The compound of claim 24 where the compound is:

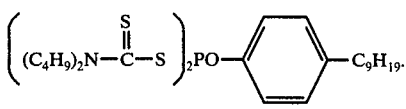

* * * * *